(12) United States Patent
King

(10) Patent No.: US 7,794,490 B2
(45) Date of Patent: Sep. 14, 2010

(54) IMPLANTABLE MEDICAL DEVICES WITH ANTIMICROBIAL AND BIODEGRADABLE MATRICES

(75) Inventor: Tamarah L. King, Haskell, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/873,338

(22) Filed: Jun. 22, 2004

(65) Prior Publication Data

US 2005/0283224 A1    Dec. 22, 2005

(51) Int. Cl.
*A61F 2/06*    (2006.01)

(52) U.S. Cl. .................................. 623/1.13; 623/1.42

(58) Field of Classification Search ....... 623/1.38–1.54, 623/1.13, 1.23, 23.72, 23.73, 23.74, 23.75, 623/23.76
See application file for complete search history.

(56) References Cited

U.S. PATENT DOCUMENTS

| | | |
|---|---|---|
| 3,142,067 A | 7/1964 | Liebig |
| 3,425,418 A | 2/1969 | Chvapil et al. |
| 3,620,218 A | 11/1971 | Schmitt et al. |
| 3,953,566 A | 4/1976 | Gore |
| 3,962,153 A | 6/1976 | Gore |
| 3,986,828 A | 10/1976 | Hoffman, Jr. et al. |
| 4,187,390 A | 2/1980 | Gore |
| 4,475,972 A | 10/1984 | Wong |
| 4,619,641 A | 10/1986 | Schanzer |
| 4,784,659 A | 11/1988 | Fleckenstein et al. |
| 5,019,096 A | 5/1991 | Fox, Jr. et al. |
| 5,116,360 A | 5/1992 | Pinchuk et al. |
| 5,163,951 A | 11/1992 | Pinchuk et al. |
| 5,213,580 A | 5/1993 | Slepian et al. |
| 5,344,455 A | 9/1994 | Keogh et al. |
| 5,527,353 A | 6/1996 | Schmitt |
| 5,609,629 A | 3/1997 | Fearnot et al. |
| 5,782,789 A | 7/1998 | Herweck et al. |
| 5,788,979 A | 8/1998 | Alt et al. |
| 5,824,049 A | 10/1998 | Ragheb et al. |

(Continued)

FOREIGN PATENT DOCUMENTS

DE    3627487 A1    2/1988

(Continued)

OTHER PUBLICATIONS

Calligaro K.D., M.D., and Frank Veith, M.D., Diagnosis and Management of Infected Prosthetic Aortic Grafts; Surgery 1991; V110-No. 5; 805-811.

(Continued)

*Primary Examiner*—Alvin J Stewart
(74) *Attorney, Agent, or Firm*—Vidas, Arrett & Steinkraus, P.A.

(57) ABSTRACT

A composite vascular graft is provided, which incorporates bioactive agents that can be controllably delivered to the implantation site to deliver therapeutic materials and/or to reduce infection of the implant. The vascular graft of the present invention includes a luminal layer of ePTFE; and a biodegradable polymer layer including a bioactive agent, such as an antimicrobial agent. The biodegradable polymer layer is posited on the external surface of the luminal ePTFE layer. The graft also includes a fabric layer, which is posited on the external surface of the biodegradable layer. The graft is particularly useful as an arterial-venous graft for hemodialysis procedures.

21 Claims, 7 Drawing Sheets

U.S. PATENT DOCUMENTS

| | | | |
|---|---|---|---|
| 5,848,995 A | 12/1998 | Walder | |
| 5,873,904 A | 2/1999 | Ragheb et al. | |
| 5,902,283 A | 5/1999 | Darouiche et al. | |
| 5,976,192 A | 11/1999 | McIntyre et al. | |
| 6,022,553 A | 2/2000 | Anders et al. | |
| 6,042,666 A * | 3/2000 | Karwoski et al. | 156/47 |
| 6,083,930 A | 7/2000 | Roufa et al. | |
| 6,162,487 A | 12/2000 | Darouiche | |
| 6,210,436 B1 | 4/2001 | Weadock | |
| 6,255,277 B1 | 7/2001 | Stamler et al. | |
| 6,296,863 B1 * | 10/2001 | Trogolo et al. | 424/404 |
| 6,315,791 B1 * | 11/2001 | Gingras et al. | 623/1.13 |
| 6,316,522 B1 * | 11/2001 | Loomis et al. | 523/105 |
| 6,328,762 B1 | 12/2001 | Anderson et al. | |
| 6,428,571 B1 | 8/2002 | Lentz et al. | |
| 6,489,446 B1 | 12/2002 | Rothstein et al. | |
| 6,540,773 B2 * | 4/2003 | Dong | 623/1.13 |
| 6,626,939 B1 * | 9/2003 | Burnside et al. | 623/1.38 |
| 6,926,735 B2 * | 8/2005 | Henderson | 623/1.42 |
| 6,939,377 B2 * | 9/2005 | Jayaraman et al. | 623/1.46 |
| 7,560,006 B2 * | 7/2009 | Rakos et al. | 156/293 |
| 2001/0056299 A1 * | 12/2001 | Thompson | 623/1.53 |
| 2002/0165601 A1 * | 11/2002 | Clerc | 623/1.13 |
| 2003/0028239 A1 * | 2/2003 | Dong | 623/1.13 |
| 2003/0050691 A1 * | 3/2003 | Shifrin et al. | 623/1.23 |
| 2003/0060871 A1 * | 3/2003 | Hill et al. | 623/1.15 |
| 2003/0097174 A1 | 5/2003 | Henderson | |
| 2003/0125796 A1 * | 7/2003 | Dong | 623/1.13 |
| 2004/0024442 A1 * | 2/2004 | Sowinski et al. | 623/1.13 |
| 2004/0033364 A1 | 2/2004 | Spiridigliozzi et al. | |
| 2004/0073293 A1 * | 4/2004 | Thompson | 623/1.19 |
| 2004/0082989 A1 * | 4/2004 | Cook et al. | 623/1.13 |
| 2004/0122507 A1 * | 6/2004 | Henderson | 623/1.27 |
| 2004/0133272 A1 * | 7/2004 | Jayaraman | 623/1.46 |
| 2004/0137066 A1 * | 7/2004 | Jayaraman | 424/486 |
| 2004/0182511 A1 * | 9/2004 | Rakos et al. | 156/287 |
| 2004/0215337 A1 * | 10/2004 | Hain et al. | 623/1.44 |
| 2005/0149173 A1 * | 7/2005 | Hunter et al. | 623/1.42 |
| 2005/0288767 A1 * | 12/2005 | Kujawski et al. | 623/1.13 |
| 2006/0094318 A1 * | 5/2006 | Matsuda et al. | 442/123 |
| 2006/0118236 A1 * | 6/2006 | House et al. | 156/294 |
| 2006/0142852 A1 * | 6/2006 | Sowinski et al. | 623/1.44 |
| 2008/0208325 A1 * | 8/2008 | Helmus et al. | 623/1.44 |
| 2009/0214615 A1 * | 8/2009 | Zhao | 424/423 |

FOREIGN PATENT DOCUMENTS

| | | |
|---|---|---|
| WO | 9014054 | 11/1990 |
| WO | 9316123 | 8/1993 |
| WO | 9419029 | 9/1994 |
| WO | 9932051 | 7/1999 |
| WO | 02100454 | 12/2002 |

OTHER PUBLICATIONS

Darouiche R.O., et al. In Vivo Efficacy of Antimicrobial-Coated Fabric from Prosthetic Heart Valve Sewing Rings. J Heart Valve Dis. 1998; V7-No. 6; 639-646.

Goodman, S.L., et al.; Platelet Interaction with Silver Treated Sewing Rings of Mechanical Heart Valves: Potential effects on Tissue Ingrowth and Healing; 24$^{th}$ Annual meeting of the Society for Biomaterials; Apr. 1998, San Diego, California, USA, p. 207.

Langanki, D., et al.; Evaluation of a Novel Bioprosthetic Heart Valve Incorporating Anticalcification and Antimicrobial Technology in a Sheep Model; J. of Heart Valve Disease; V7, No. 6, 1998; 633-638.

Tweten, K.S., Biocompatability of Silver-Modified Polyester for Antimicrobial Protection of Prosthetic Valves; J. of Heart Valve Disease; V6, No. 5, 1997; pp. 554-561.

Weiler, A., M.D. et al.; Biodegradable Implants in Sports Medicine: The Biological Base; Arthroscopy: The Journal of Arthroscopic and Related Surgery; vol. 16, No. 3 (Apr. 2000), pp. 305-321.

Middleton, John C. and Tipton, Arthur J.; Synthetic Biodegradable Polymers as Medical Devices; Medical Plastics and Biomaterials Magazine, Mar. 1998; internet site: http://www.devicelink.com/mpb/archive/98/03/002.html.

Annex dated Dec. 30, 2003 from EPO on-line file for EP1399200.

Schanzer et al., "A self-sealing dialysis prosthesis" Annals of Surgery, Nov. 1986; 204(5): 574-9.

Technical data demonstrating penetration of adhesive into ePTFE substrates using the method of D3(W094-19029) dated Apr. 5, 2007.

* cited by examiner

IMPLANTABLE MEDICAL DEVICES WITH ANTIMICROBIAL AND BIODEGRADABLE MATRICES

FIELD OF THE INVENTION

The present invention relates to implantable medical devices, which inhibit or reduce bacterial growth during their use in a living body. More particularly, the present invention relates to composite vascular grafts which incorporate bioactive agents to deliver therapeutic materials and/or to inhibit or reduce bacterial growth during and following implantation, and which also desirably incorporate a luminal layer of ePTFE with an internodal distance of 70-90 microns to allow for intercellular communication.

BACKGROUND OF THE INVENTION

Poor glycemic control in diabetes and hypertension can lead to the requirement for hemodialysis. In order to facilitate treatment, a significant number of patients with these disorders will have a synthetic vascular graft surgically implanted between the venous and arterial systems to allow arterial-venous (A-V) access at the implantation type. The average time a synthetic graft will remain useful for A-V access is about two years. During these two years, infection will develop in around 20% of patients, and often leads to graft removal. The hemodialysis access then has to be reestablished. Often, this means finding another site for A-V access and waiting a period of time of three weeks before a normal hemodialysis schedule can be resumed. It is known that 15-30% of all dialysis patients will have infection of their implant as a major cause of death.

There are principally three ways in which an infection can be introduced during A-V access set up or the hemodialysis procedure itself. For example, bacteria can be implanted with the A-V access device itself during a break in aseptic technique. Another way is through the attachment of bacteria which are already internally present onto the surface of the device. Moreover, bacteria can be transmitted from external sources, such as central venous catheters and needles. The major cause in infection involving A-V access PTFE grafts has been shown to be due to a break in aseptic cannulation. The port of entry for infection is typically the puncture site or catheter.

The most common infectious agents are: *staphylococcus aureus, pseudomonas aeruginosa*, and *staphylococcus epidermis*. These agents have been identified in over 75% of all reported vascular infections. Both *staphylococcus aureus* and *pseudomonas aeruginosa*, show high virulence and can lead to clinical signs of infection early in the post-operative period (less than four months). It is this virulence that leads to septicemia and is one main factor in the high mortality rates. *Staphylococcus epidermis* is described as a low virulence type of bacterium. It is late occurring, which means it can present clinical signs of infection up to five years post-operative. This type of bacterium has been shown to be responsible for up to 60% of all vascular graft infections. Infections of this type often require total graft excision, debridement of surrounding tissue, and revascularization through an uninfected route.

Such high virulence organisms are usually introduced at the time of implantation. For example, some of the *staphylococcus* strains (including *staphylococcus aureus*) have receptors for tissue ligands such as fibrinogen molecules which are among the first deposits seen after implantation of a graft. This tissue ligand binding provides a way for the bacteria to be shielded from the host immune defenses as well as systemic antibiotics. The bacteria can then produce polymers in the form of a polysaccharide that can lead to a slime layer on the outer surface of the graft. In this protective environment, bacterial reproduction occurs and colonies form within the biofilm that can shed cells to surrounding tissues (Calligaro, K. and Veith, Frank, Surgery, 1991 V110-No. 5, 805-811). Infection can also originate from transected lymphatics, from inter-arterial thrombus, or be present within the arterial wall.

There are severe complications as a result of vascular graft infections. For example, anastonomic disruption due to proteolytic enzymes that the more virulent organisms produce can lead to a degeneration of the arterial wall adjacent to the anastomosis. This can lead to a pseudoaneurism which can rupture and cause hemodynamic instability. A further complication of a vascular graft infection can be distal styptic embolisms, which can lead to the loss of a limb, or aortoenteric fistulas, which are the result of a leakage from a graft that is infected and that leads to gastrointestinal bleeding (Greisler, H., Infected Vascular Grafts. Maywood, Ill., 33-36).

Desirably, it would be beneficial to prevent any bacteria from adhering to the graft, or to the immediate area surrounding the graft at the time of implantation. It would further be desirable to prevent the initial bacterial biofilm formation described above by encouraging normal tissue ingrowth within the tunnel, and by protecting the implant itself from the biofilm formation.

Silver has been shown in vitro to inhibit bacterial growth in several ways. For example, it is known that silver can interrupt bacterial growth by interfering with bacterial replication through a binding of the microbial DNA, and also through the process of causing a denaturing and inactivation of crucial microbial metabolic enzymes by binding to the sulfhydryl groups (Tweten, K., J. of Heart Valve Disease 1997, V6, No. 5, 554-561). It is also known that silver causes a disruption of the cell membranes of blood platelets. This increased blood platelet disruption leads to increased surface coverage of the implants with platelet cytoskeletal remains. This process has been shown to lead to an encouragement of the formation of a more structured (mature state) pannus around the implant. This would likely discourage the adhesion and formation of the biofilm produced by infectious bacteria due to a faster tissue ingrowth time (Goodman, S. et al, 24th Annual Meeting of the society for Biomaterials, April 1998, San Diego, Calif.; pg. 207).

It is known to incorporate antimicrobial agents into a medical device. For example, prior art discloses an ePTFE vascular graft, a substantial proportion of the interstices of which contain a coating composition that includes: a biomedical polyurethane; poly(lactic acid), which is a biodegradable polymer; and the anti-microbial agents, chlorhexidine acetate and pipracil. The prior art further describes an ePTFE hernia patch which is impregnated with a composition including silver sulfadiazine and chlorhexidine acetate and poly(lactic acid).

Further prior art describes a medical implant wherein an antimicrobial agent penetrates the exposed surfaces of the implant and is impregnated throughout the material of the implant. The medical implant may be a vascular graft and the material of the implant may be polytetrafluoroethylene (PTFE). The antimicrobial agent is selected from antibiotics, antiseptics and disinfectants.

Moreover, there is prior art that discloses that silver, which is a known antiseptic agent, can be deposited onto the surface of a porous polymeric substrate via silver, ion assisted beam deposition prior to filling the pores of the porous polymeric material with an insoluble, biocompatible, biodegradable material. This prior art further discloses that antimicrobials can be integrated into the pores of the polymeric substrate. The substrate may be a porous vascular graft of ePTFE.

It is known that multiple layers in grafts can be effective in providing a differential cross-section of permeability and/or porosity to achieve enhanced healing and tissue ingrowth. In addition, attempts to increase the radial tensile and axial tear strengths of porous tubular grafts include placing multiple layers over one another. Prior art describing composite, anti-infective medical devices will now be discussed.

It is known to provide an anti-infective medical article including a hydrophilic polymer having silver chloride bulk distributed therein. The hydrophilic polymer may be a laminate over a base polymer. Preferred hydrophilic polymers are disclosed as melt processible polyurethanes. The medical article may be a vascular graft. A disadvantage of this graft is that it is not formed of ePTFE, which is known to have natural antithrombogenic properties. A further disadvantage is that the hydrophilic polyurethane matrix into which the silver salt is distributed does not itself control the release of silver into the surrounding body fluid and tissue at the implantation site of the graft.

Furthermore, there is prior art describing an implantable medical device that can include a stent structure, a layer of bioactive material posited on one surface of the stent structure, and a porous polymeric layer for controlled release of a bioactive material which is posited over the bioactive material layer. The thickness of the porous polymeric layer is described as providing this controlled release. The medical device can further include another polymeric coating layer between the stent structure and the bioactive material layer. This polymeric coating layer is disclosed as preferably being formed of the same polymer as the porous polymeric layer. Silver can be included as the stent base metal or as a coating on the stent base metal. Alternatively, silver can be in the bioactive layer or can be posited on or impregnated in the surface matrix of the porous polymeric layer. Polymers of polytetrafluoroethylene and bioabsorbable polymers can be used. A disadvantage of this device is that the porous polymeric outer layer needs to be applied without the use of solvents, catalysts, heat or other chemicals or techniques, which would otherwise degrade or damage the bioactive agent deposited on the surface of the stent. Moreover, this graft is not designed to achieve fast tissue ingrowth within the tunnel to discourage initial bacterial biofilm formation.

Further prior art describes a vascular graft made with a porous antimicrobial fabric formed by fibers which are laid transverse to each other, and which define pores between the fibers. The fibers may be of ePTFE. Ceramic particles are bound to the fabric material, the particles including antimicrobial metal cations thereon, which may be silver ions. The ceramic particles are exteriorly exposed and may be bound to the graft by a polymeric coating material, which may be a biodegradable polymer. A disadvantage of this device is that the biodegradable coating layer does not provide sufficient tensile strength for an outer graft layer. Moreover, this graft does not include a polymeric ePTFE tube, which has certain advantages over conventional textile prostheses. For example, a polymeric ePTFE tube has a microporous structure consisting of small nodes interconnected with many thin fibrils. The diameter of the fibrils, which depend on the processing conditions, can be controlled to a large degree, and the resulting flexible structure has greater versatility. For example, it can be used in both large diameter, i.e. 6 mm or greater artificial blood vessels, as well as in grafts having diameters of 5 mm or less.

There is a need for additional antimicrobial vascular grafts formed of ePTFE. In particular, there is a need for ePTFE multi-layered vascular grafts which incorporate antimicrobial agents that can be controllably released from biodegradable materials in the graft to suppress infection following implantation and to prevent biofilm formation. It would also be desirable to provide such grafts with sufficient tensile strength in the tissue-contacting outer layer and with good cellular communication between the blood and the perigraft tissue in the luminal layer.

SUMMARY OF THE INVENTION

The present invention solves a need in the art by providing a vascular graft which can deliver one or more bioactive agents to the region of a blood vessel in a controlled fashion. In desired embodiments, the bioactive agents include an antimicrobial agent to inhibit or reduce infection during and following the introduction of the graft to the implantation site in the body. The inventive vascular graft is a composite device including three separate layers. For example, the invention provides a vascular graft including a luminal layer of ePTFE; and a biodegradable polymer layer, which includes at least one bioactive agent. The biodegradable layer is posited on the external surface of the luminal ePTFE layer. The inventive graft further includes a fabric layer, which is posited on the external surface of the biodegradable layer.

The invention further provides a vascular graft including a luminal layer of ePTFE with an internodal distance (IND) of up to about 90 microns and, desirably, about 70 to about 90 microns; and a biodegradable polymer layer that includes an antimicrobial agent, the biodegradable layer being posited on the external surface of the luminal layer. This graft also includes a fabric layer posited on the external surface of the biodegradable layer, wherein the fabric layer is of sufficient porosity to allow tissue ingrowth to replace the biodegradable polymer layer upon hydrolysis thereof.

Preferably, the biodegradable polymer is hydrophilic with a swelling capacity up to 300%. The bioactive agent(s) placed within the biodegradable polymer of the medial layer are controllably released from the medial layer to the blood and surrounding tissue at the implantation site. In particular, the rate of elution of the bioactive agent is controlled by the rate of hydrolysis of a biodegradable polymer. Desirably, the bioactive agent is a silver agent. The silver prevents bacteria from adhering to the graft, or to the area surrounding the graft at the time of implantation and prevents initial bacterial biofilm formation by encouraging tissue ingrowth within the tunnel, and by protecting the implant itself from biofilm formation.

The outer tissue-contacting fabric layer adds tensile strength to the graft and is of a porosity which allows sufficient tissue ingrowth to replace the structure of the hydrolyzed biodegradable layer. The fabric layer further serves to encourage tissue growth within the outer surfaces of the graft, which discourages biofilm formation around the graft.

The IND of 70 to 90 microns in the luminal ePTFE layer allows for cellular communication between the blood and the perigraft tissue. It also encourages normal tissue ingrowth within the tunnel to discourage biofilm formation.

The present invention also provides a method of making a vascular graft for controllable delivery of a bioactive agent associated therewith to a site of implantation of the graft. The method includes the following steps: providing a luminal layer of ePTFE; positing a biodegradable polymer layer including a bioactive agent on the external side of the luminal layer; and positing a fabric layer on the external surface of the biodegradable layer.

BRIEF DESCRIPTION OF THE DRAWINGS

FIG. 7A depicts a diamond braid, FIG. 7B depicts a regular braid and FIG. 7C depicts a Hercules braid.

DETAILED DESCRIPTION OF THE INVENTION

In preferred embodiments of the present invention, the implantable composite device is a multi-layered tubular structure which is particularly suited for use as an arterial-venous (AV) graft. The prosthesis preferably includes at least one extruded polytetrafluoroethylene (PTFE) tube. PTFE exhibits superior biocompatibility and is suitable for vascular applications as the result of its low thrombogenicity. Furthermore, the prosthesis includes a biodegradable polymeric material which is preferably applied as a coating layer to the ePTFE tube, and which is designed to regulate delivery of a bioactive agent associated therewith to the site of implantation. In a desired embodiment, the bioactive agent is an antimicrobial agent, such as a silver agent. In particular, the rate of elution of the silver agent is controlled by the rate of hydrolysis of the biodegradable polymer. The prosthesis preferably also includes a third tube of fabric that provides tensile strength to the graft and that has a porosity sufficient to permit a sufficient tissue ingrowth to replace the polymer structure of the biodegradable layer following hydrolysis.

Figure 1:
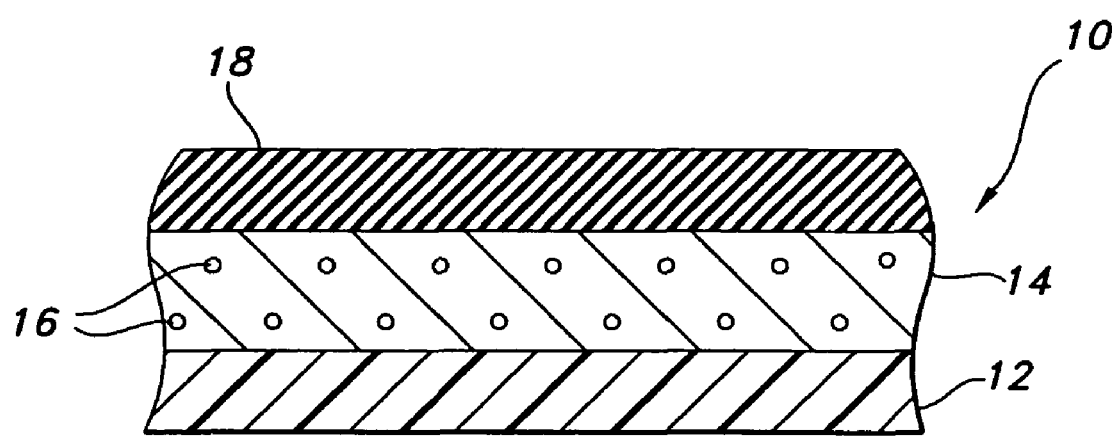
FIG. 1 is a schematic longitudinal cross-sectional representation of an embodiment of the vascular graft of the present invention.

FIG. 1 shows vascular graft 10 of the present invention. As noted above, the present invention takes the preferred embodiment of a composite tubular graft, wherein the layers are shown in FIG. 1, which represent the tubular members forming the composite structure. However, it may be appreciated that the present invention also contemplates other implantable multi-layer prosthetic structures such as vascular patches, blood filters, film wraps for implantable devices such as stents, hernia repair fabrics and plugs and other such devices where such structures may be employed. As shown in FIG. 1, the composite device 10 of the present invention includes a luminal ePTFE layer 12 and a biodegradable layer 14 overlaying the luminal layer 12. Biodegradable layer 14 permits controlled delivery of bioactive agents 16 associated with layer 14 therethrough. Device 10 of the present invention further includes a textile fabric layer 18, which provides radial tensile strength at the outermost tube and permits tissue ingrowth.

Figure 2:
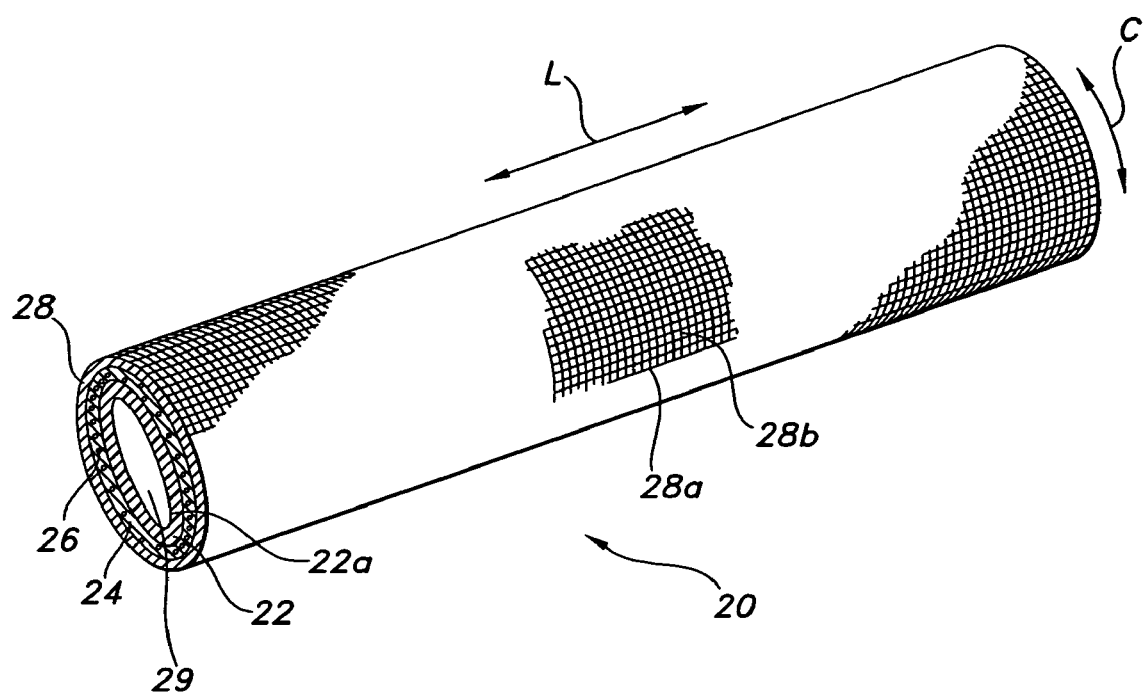
FIG. 2 is a perspective view of a tubular vascular graft according to the present invention.

Referring now to FIG. 2, a preferred embodiment of a composite tubular graft of the present invention is shown, wherein the layers shown in FIG. 1 represent the tubular members in FIG. 2 forming the composite structure. Device 20 includes an inner ePTFE tubular member 22 and a medial biodegradable coating layer 24 disposed coaxially thereover. Biodegradable layer 24 includes a bioactive agent 26 which is preferably distributed substantially evenly throughout the bulk of the biodegradable matrix of layer 24. An outer tubular textile fabric member 28 is disposed coaxially over biodegradable layer 24. As will be described in further detail below, virtually any textile construction can be used for the fabric layer 28, including weaves, knits, braids, filament windings, spun fibers and the like. Any weave pattern in the art, including, simple weaves, basket weaves, twill weaves, velour weaves and the like may be used. The weave pattern shown in FIG. 2 includes warp yarns 28a running along the longitudinal length (L) of the graft and fill yarns 28b running around the circumference (C) of the graft, the fill yarns being at approximately 90 degrees to one another with fabrics flowing from the machine in the warp direction. A central lumen 29 extends throughout the tubular composite graft 20 defined further by the inner wall 22a of luminal tube 22, which permits the passage of blood through graft 20 once the graft is properly implanted in the vascular system.

Figure 3:
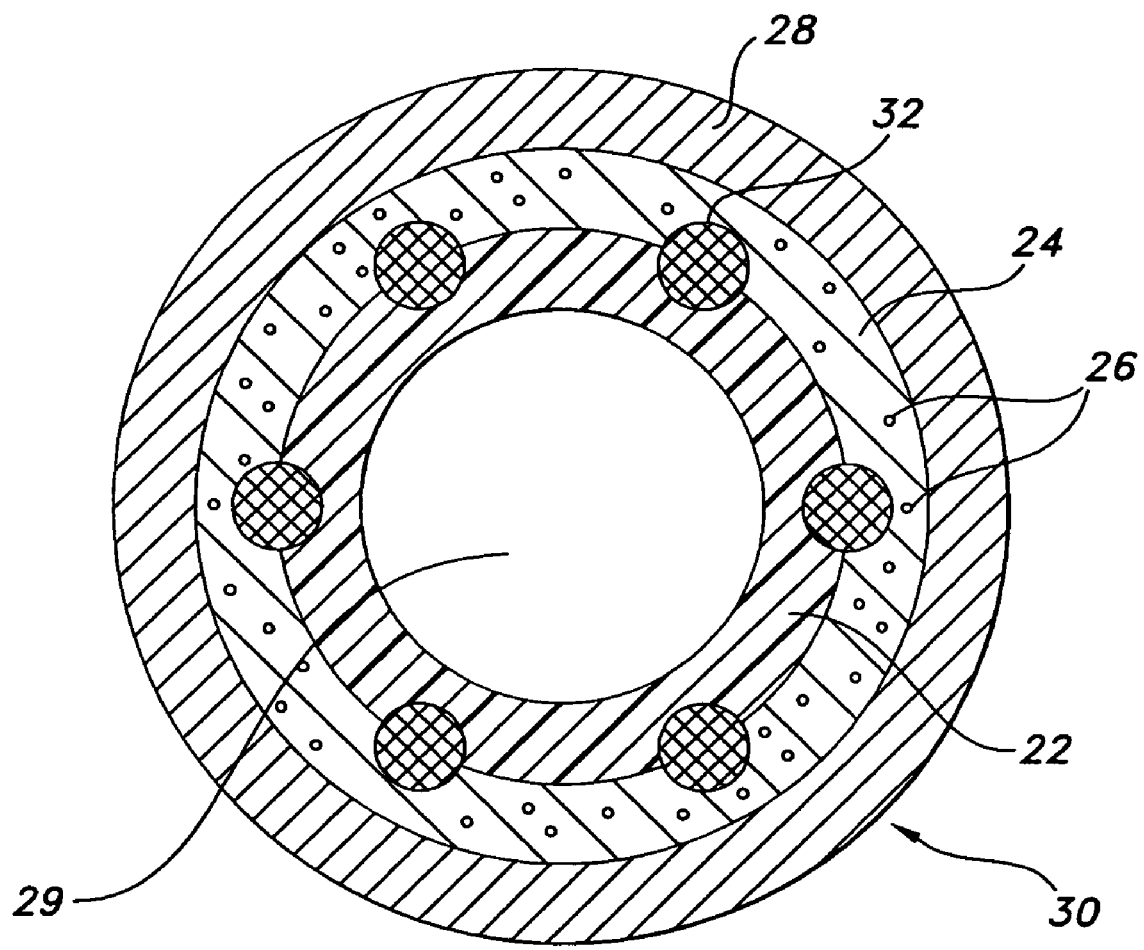
FIG. 3 is a cross-sectional showing of an embodiment of a stent/graft composite of the present invention.

It is well within the contemplation of the present invention that a stent can be interposed between the layers of the graft of the present invention. With reference to FIG. 3, a stent/graft composite device 30 of the present invention is shown. Device 30 includes inner ePTFE tubular member 22 and medial, biodegradable layer 24 disposed coaxially thereover. As described above, biodegradable layer 24 includes a bioactive agent 26, such as a silver agent, which can be controllably released from biodegradable layer 24. This controllable release is dependent on the rate of hydrolysis of the bonds within biodegradable layer 24. Composite device 30 further includes fabric tubular member 28 which is disposed coaxially over biodegradable layer 24. Central lumen 29 extends throughout tubular composite graft 30. An expandable stent 32 may be interposed between inner ePTFE tubular member 22 and biodegradable layer 24. Stent 32, which may be associated with the graft of the present invention, is used for increased support of the blood vessel and increased blood flow through the area of implantation. It is noted that increased radial tensile strength at the outer tubular fabric member 28 enables the graft to support, for example, radial expansion of stent 32, when present.

In order to facilitate hemodialysis treatment, a significant number of patients suffering from hypertension or poor glycemic control in diabetes will have a synthetic vascular graft surgically implanted between the venous and arterial systems. Typically, these grafts become occluded over time. In these instances, a covered stent across the venous anastomotic site in patients with significant stenosis may aid in prolonging the patency of these grafts, which would avoid painful and typically expensive surgical revisions. For these reasons, it is well within the contemplation of the present invention that a stent covered with or incorporated within the vascular graft of the present invention may be useful for AV access.

As noted above, in one aspect of the present invention, composite device 10, which in desired embodiments is an AV graft, includes an ePTFE luminal layer 12 depicted in FIG. 1. PTFE exhibits superior biocompatibility and low thrombogenicity, which makes it particularly useful as vascular graft material. Desirably, the ePTFE layer is a tubular structure 22, as depicted in FIG. 2. The ePTFE material has a fibrous state which is defined by interspaced nodes interconnected by elongated fibrils. The space between the node surfaces that is spanned by the fibrils is defined as the internodal distance. In the present invention, the internodal distance in the luminal ePTFE layer is desirably greater than 40 microns, and in particular, about 70 to about 90 microns. When the term "expanded" is used to describe PTFE, i.e. ePTFE, it is intended to describe PTFE which has been stretched, in accordance with techniques which increase the internodal distance and concomitantly porosity. The stretching may be done uni-axially, bi-axially, or multi-axially. The nodes are stretched apart by the stretched fibrils in the direction of the expansion.

Figure 4:
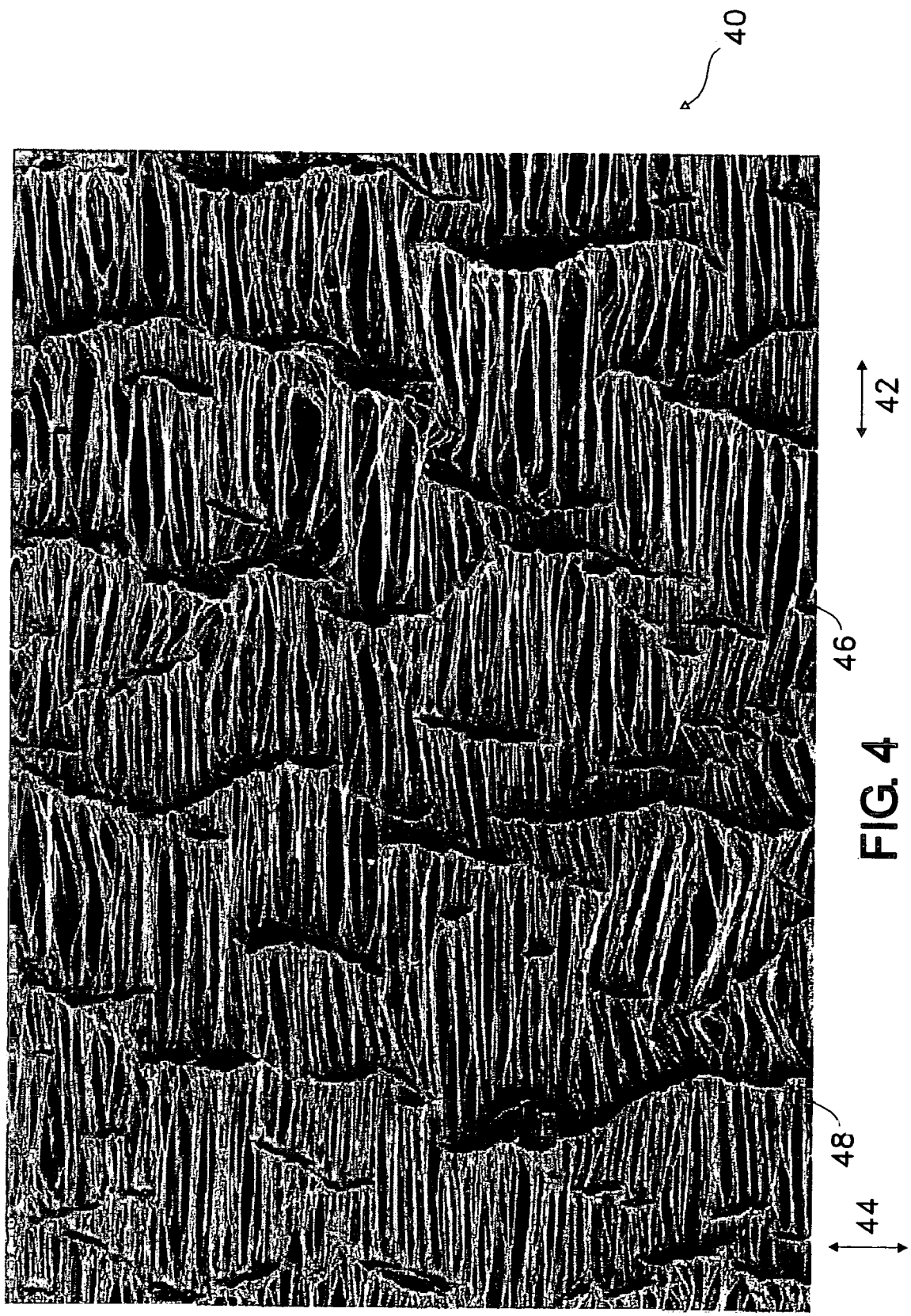
FIG. 4 is a photomicrograph showing a longitudinally expanded ePTFE structure.

FIG. 4 is a photomicrograph of a traditionally longitudinally expanded ePTFE tubular structure 40. The tube has been stretched in the longitudinal direction shown by directional arrow 42, leaving the nodes circumferentially oriented in circumferential direction shown by the directional arrow 44. The fibrils 46 are shown as being uniformly oriented in the longitudinal direction shown by directional arrow 42. Nodes 48 are shown are oriented in circumferential direction 44. Methods of making conventional longitudinally expanded ePTFE are well known in the art.

It is further contemplated that the ePTFE may be a physically modified ePTFE tubular structure having enhanced axial elongation and radial expansion properties of up to 600% by linear dimension. The physically modified ePTFE tubular structure is able to be elongated or expanded and then returned to its original state without an elastic force existing therewithin. Additional details of physically-modified ePTFE and methods for making the same can be found in commonly assigned Application Title "ePTFE Graft With Axial Elongation Properties", assigned U.S. application Ser. No. 09/898,418, filed on Jul. 3, 2001, published on Jan. 9, 2003 as U.S. Application Publication No. 2003-0009210A1, the contents of which are incorporated by reference herein in its entirety.

A further aspect of the composite device of the present invention relates to the biodegradable, medial layer shown as layer 14 in FIG. 1. The biodegradable layer may be comprised of natural, modified natural or synthetic polymers, copolymers, block polymers, as well as combinations thereof. Preferably, the biodegradable polymer is hydrophilic with a swelling capacity up to 300%. It is noted that a polymer is generally named based on the monomer it is synthesized from. Examples of suitable biodegradable polymers or polymer classes include fibrin, collagen, elastin, celluloses, gelatin, vitronectin, fibronectin, laminin, reconstituted basement membrane matrices, starches, dextrans, alginates, hyaluronic acid, poly(lactic acid), poly(glycolic acid), polypeptides, glycosaminoglycans, their derivatives and mixtures thereof. For both glycolic acid and lactic acid, an intermediate cyclic dimer is typically prepared and purified, prior to polymerization. These intermediate dimers are called glycolide and lactide, respectively.

Other useful biodegradable polymers or polymer classes include the following: polydioxanones, polyoxalates, poly (α-esters), polyanhydrides, polyacetates, polycaprolactones, poly(orthoesters), polyamino acids, polyamides and mixtures and copolymers thereof.

Additional useful biodegradable polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific biodegradable polymers which are useful include those marketed under the Biodel and Medisorb trademarks. The Biodel materials represent a family of various polyanhydrides which differ chemically. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

In one desirable aspect of the invention, the polymer used to form the biodegradable layer is a hydrogel. More desirably, the hydrogel is produced from a synthetic polymeric material. Such synthetic polymers can be tailored to a range of properties and predictable lot-to-lot uniformity, and represent a reliable source of material and one generally free from concerns of immunogenicity. In general, hydrogels are polymeric materials that can absorb more than 20% of their weight in water while maintaining a distinct three-dimensional structure. This definition includes dry polymers that will swell in aqueous environments, as well as to water-swollen materials. A host of hydrophilic polymers can be cross-linked to produce hydrogels, whether the polymer is of biological origin, semi-synthetic, or wholly synthetic. Hydrogels can be grafted, bonded or otherwise affixed onto substrate materials, such as ePTFE. Properties that make hydrogels valuable in drug delivery applications include the equilibrium swelling degree, sorption kinetics, solute permeability, and their in vivo performance characteristics. Permeability to various solutes, including silver agents, depends in part upon the swelling degree or water content and the rate of biodegradation. Since the mechanical strength of a gel declines in direct proportion to the swelling degree, the hydrogel can be attached to the ePTFE luminal layer so that the composite system enhances mechanical strength. A preferred hydrogel for use in the present invention is a water insoluble copolymer having a hydrophilic region, at least two functional groups that will allow for cross-linking of the polymer chains, and a bioresorbable hydrophobic region.

In general, a suitable biodegradable polymer for use in the biodegradable medial layer of the composite device of the present invention is desirably configured so that it has mechanical properties that match the application, remaining sufficiently intact until the surrounding tissue has in-grown and healed, does not invoke an inflammatory or toxic response, is metabolized in the body after fulfilling its purpose, leaving no trace, is easily processible into the final product formed, demonstrates acceptable shelf-life, and is easily sterilized.

Factors affecting the mechanical performance of in vivo biodegradable polymers are well known to the polymer scientist, and include monomer selection, initial process conditions, and the presence of additives. Biodegradation has been accomplished by synthesizing polymers that have unstable linkages in the backbone, or linkages that can be safely oxidized or hydrolyzed in the body. The most common chemical functional groups having this characteristic are ethers, esters, anhydrides, orthoesters and amides. It is noted that the biodegradable layer need not be comprised entirely of the biodegradable material.

As described above, the biodegradable layer can include an antimicrobial agent, such as a silver agent. Silver has been shown to possess antimicrobial activity and is generally present in the devices of the present invention in amounts sufficient to provide antimicrobial effects. In preferred embodiments, the silver agent comprises silver metal ions. These silver ions are believed to exert their effects by disrupting respiration and electron transport systems upon absorption into bacterial or fungal cells. Antimicrobial silver ions are useful for in vivo use because they are not substantially absorbed into the body, and typically pose no hazard to the body.

In one aspect of the invention, the silver metal ion can be selected from the following: silver iodate, silver iodide, silver nitrate, and silver oxide. The silver metal ion is desirably present in the range of from about 0.5% to about 2 wt. % of a hydrogel in the biodegradable layer.

The bioactive agent (e.g., a silver agent) is desirably evenly distributed throughout the bulk of the biodegradable layer and is controllably released from the biodegradable layer to the site of implantation of the graft by hydrolysis of chemical bonds in the biodegradable polymer.

A solution of biodegradable material that includes a monomer (or an intermediate cyclic dimer) on which the biodegradable polymer is based can be applied as a coating to the external side of the ePTFE luminal layer. This can be accomplished by such means as dipping, spraying, painting, etc. A silver agent or other bioactive agent can be blended into the wet or fluid biodegradable material to form a coating mixture which is then applied to the luminal layer by a spraying process, for example. Alternatively, a silver agent or other bioactive agent may be applied in powdered form to wet or fluid biodegradable material after the biodegradable material has been applied as a coat to the luminal layer, but before it solidifies.

As used herein, "solidified" means that the biodegradable material is precipitated out to solid form. The biodegradable material is desirably cross-linked to accomplish solidification. Alternatively, this solidification can be accomplished by other standard chemical reactions that are compatible with the present invention.

In preparing the biodegradable medial layer, a solution or fluid of a biocompatible, biodegradable material can be formed for application to the external surface of the ePTFE luminal layer. For example, extracellular matrix proteins which are used in fluid/solution may be soluble. However some materials may be difficult to dissolve in water. Collagen, for example, is considered insoluble in water, as is gelatin at ambient temperature. To overcome such difficulties, collagen or gelatin may preferably formed at an acidic pH, i.e. at a pH less than 7 and, preferably, at a pH of about 2 to about 4. The temperature range at which such fluid/solutions are formed is between about 4° C. to about 40° C., and preferably about 30° C.-35° C.

In situations where the bioactive agent is insoluble in the wet or fluid biodegradable polymer material, the agent may be finely subdivided as by grinding with a mortar and pestle. For example, a silver agent can be micronized to yield a product wherein some or all particles are the size of about 5 microns or less. The finely subdivided silver agent can then be distributed desirably substantially evenly throughout the bulk of the wet or fluid biodegradable layer before cross-linking or cure solidifies the layer.

It is well within the contemplation of the present invention that the biodegradable layer can be combined with various carrier, drug, prognostic, diagnostic, or therapeutic materials. For example, the biodegradable layer can be combined with any of the following bioactive agents: antimicrobial agents (such as silver agents, chlorhexidine, triclosan, iodine, and benzalkonium chloride); anti-thrombogenic agents, such as heparin, heparin derivatives, urokinase, and PPack (dextrophenylalanine proline, arginine, chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents, such as dexamethasone, prednisolone, corticosterone, budesonide, estrogen, sulfasalazine, and mesalamine); anti-neoplastics/anti-proliferative/anti-miotic agents (such as paclitaxel, 5-flurouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bi-functional molecules consisting of a growth factor and a cytotoxin, bi-functional molecules consisting of an antibody and a cytotoxin); cholesterol-lowering agents; vasodilating agents; and agents which interfere with andogenous or vasoactive mechanisms. In addition, cells which are able to survive within the body and are dispersed within the biodegradable layer may be therapeutically useful. These cells themselves may be therapeutically useful or they may be selected or engineered to produce and release therapeutically useful compositions.

In other embodiments, bioactive agents associated with the composite device of the present invention may be genetic agents. Examples of genetic agents include DNA, anti-sense DNA, and anti-sense RNA. DNA encoding one of the following may be particularly useful in association with an implantable device according to the present invention: (a) tRNA or RRNA to replace defective or deficient endogenous molecules; (b) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor; (c) cell cycle inhibitors; (d) thymidine kinase and other agents useful for interfering with cell proliferation; and (e) the family of bone morphogenic proteins. Moreover, DNA encoding molecules capable of inducing an upstream or downstream effect of a bone morphogenic protein may be useful.

In another aspect of the present invention, composite device 10 in FIG. 1 includes fabric layer 18, which is exposed on the external surface of biodegradable layer 14. The fabric layer is added for tensile strength and is of sufficient porosity to allow sufficient tissue ingrowth to replace the structure of the biodegradable polymer as it is hydrolyzed. Any type of textile products can be used as yarns for a fabric layer. Of particular usefulness in forming a fabric layer for the composite device of the present invention are synthetic materials such as synthetic polymers. Synthetic yarns suitable for use in the fabric layer include, but are not limited to, polyesters, including PET polyesters, polypropylenes, polyethylenes, polyurethanes and polytetrafluoroethylenes. The yarns may be of the mono-filament, multi-filament, spun-type or combinations thereof. The yarns may also be flat, twisted or textured, and may have high, low or moderate shrinkage properties or combinations thereof. Additionally, the yarn type and yarn denier can be selected to meet specific properties desired for the prosthesis, such as porosity and flexibility. The yarn denier represents the linear density of the yarn (number of grams mass divided by 9,000 meters of length). Thus, a yarn with a small denier would correspond to a very fine yarn, whereas a yarn with a large denier, e.g., 1,000, would correspond to a heavy yarn. The yarns used for the fabric layer of the device of the present invention may have a denier from about 20 to about 200, preferably from about 30 to about 100. Desirably, the yarns are polyester, such as polyethylene terephthalate (PET). Polyester is capable of shrinking during a heat-set process, which allows it to be heat-set on a mandrel to form a generally circular shape.

After forming the fabric layer of the present invention, it is optionally cleaned or scoured in a basic solution of warm water. The textile is then rinsed to remove any remaining detergent, and is then compacted or shrunk to reduce and control in part the porosity of the fabric layer. Porosity of a textile material is measured on the Wesolowski scale and by the procedure of Wesolowski. In this test, a fabric test piece is clamped flatwise and subjected to a pressure head of about 120 mm of mercury. Readings are obtained which express the number of mm of water permeating per minute through each square centimeter of fabric. A zero reading represents absolute water impermeability and a value of about 20,000 represents approximate free flow of fluid.

The porosity of the fabric layer is often about 7,000 to about 15,000 on the Wesolowski scale. A more desirable porosity is from about 30 to about 5,000 on the Wesolowski scale. Most desirably, the porosity is from about 5,000 to about 17,000 on this scale to permit tissue ingrowth, while retaining tensile strength in the outer layer. The fabric layer may be compacted or shrunk in the wale direction to obtain the desired porosity. A solution of organic component, such as hexafluoroisopropanol or trichloroacetic acid, and a halogenated aliphatic hydrocarbon, such as methylene chloride, can be used to compact the textile graft by immersing it into the solution for up to 30 minutes at temperatures from about 15° C. to about 160° C.

Yarns of the fabric layer may be one ply or multi-ply yarns. Multi-ply yarns may be desirable to impart certain properties onto the drawn yarn, such as higher tensile strengths for the outer fabric layer.

Figure 5:
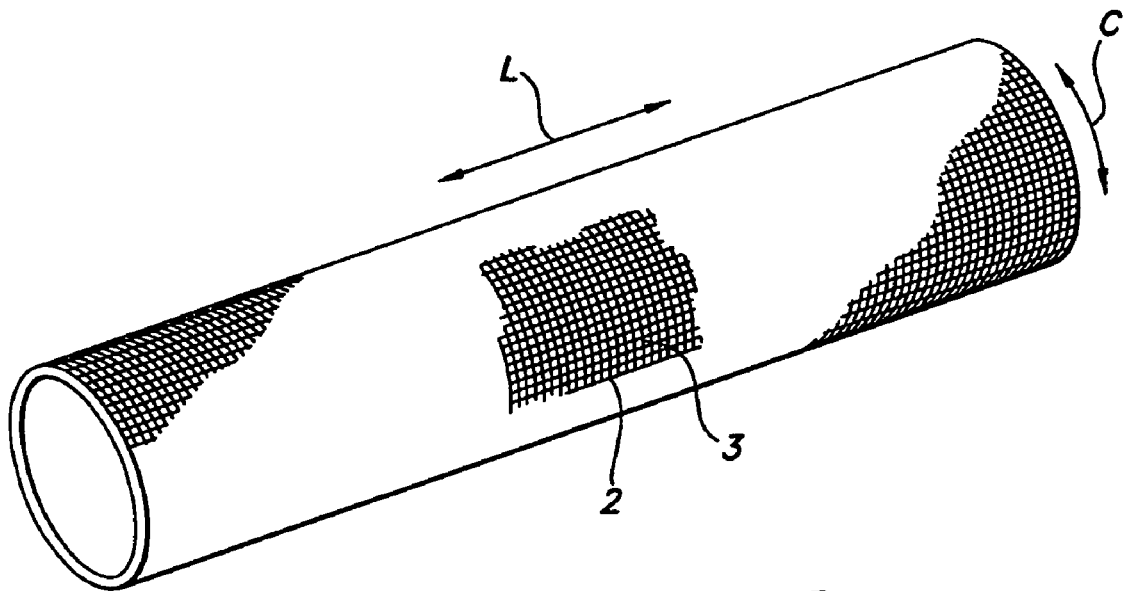
FIG. 5 is a perspective view of a fabric layer useful in the graft of the present invention.
Figure 6:
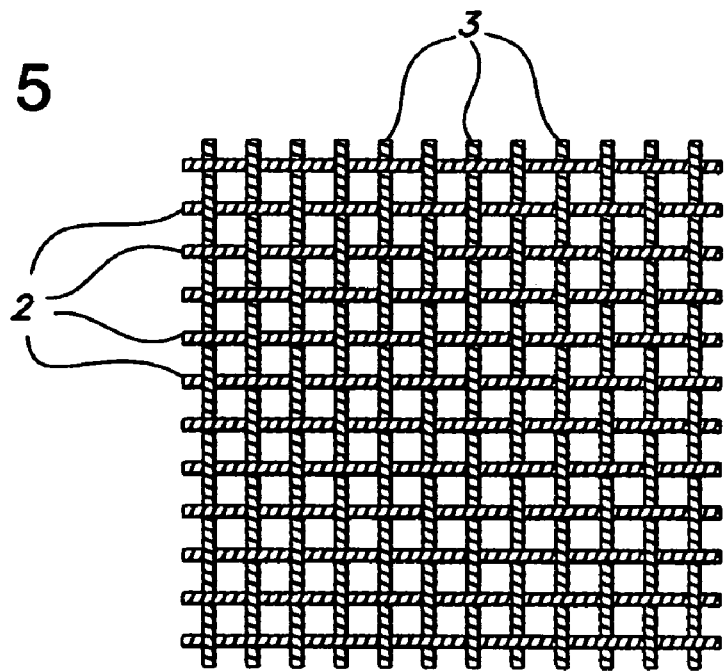
FIG. 6 is a schematic showing of a conventional weave pattern useful for the fabric layer of the graft of the present invention.
Figure 7:
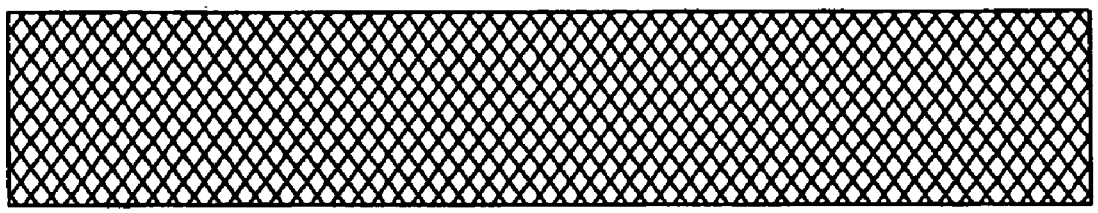
FIG. 7 is a side elevation view of a braided fabric layer useful in the graft of the present invention.
Figure 7A:
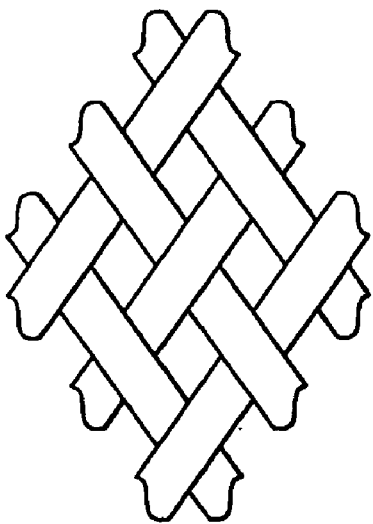
FIGS. 7A-7C are schematic showings of various types of braids that can be used in the braided fabric layer of FIG. 7.
Figure 7B:
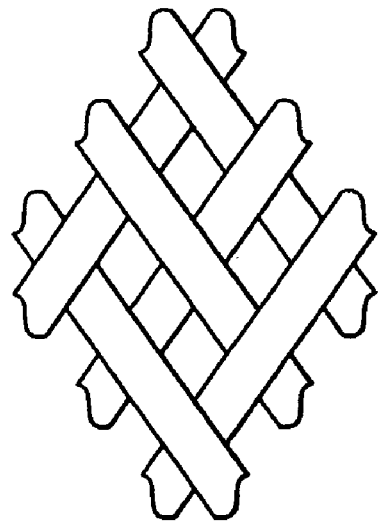
Figure 7C:
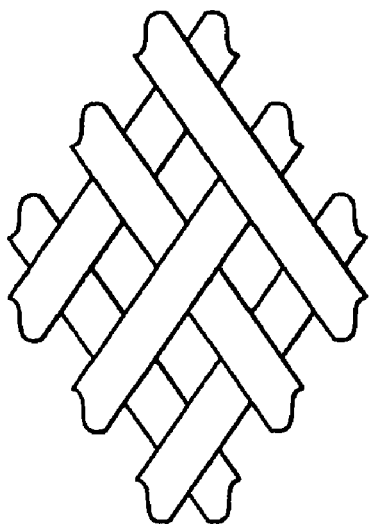

It is well within the contemplation of the present invention that the yarns of the fabric layer can have virtually any textile construction, including weaves, knits, braids, filament windings, spun fibers and the like. For example, with reference to FIGS. 5 and 6, a woven tubular prosthesis is shown. Any known weave pattern for the fabric layer may be used, including simple weaves, basket weaves, twill weaves, velour weaves and the like may be used. The weave pattern includes warp yarns 2 running along the longitudinal length (L) of the woven product and fill yarns 3 running around the circumference (C) of the woven product. The warp and fill yarns are at approximately 90 degrees to one another with fabric flowing from the machine in the warp direction.

Braiding may also be used, as shown for example in FIGS. 7 and 7A-7C. Braiding of yarns includes the interlacing of a two yarn systems, such as the pass of the yarns are diagonal to the fabric delivery direction, forming either flat or tubular structure. Useful braids include an interlocking three-dimensional braid and a solid three-dimensional braid. A multi-layered braided structure is defined as a structure formed by braiding wherein the structure has a plurality of distinct and discrete layers. These layers may be bound by interlocking yarns or by adhesive laminates, sewing or the like.

Figure 8:
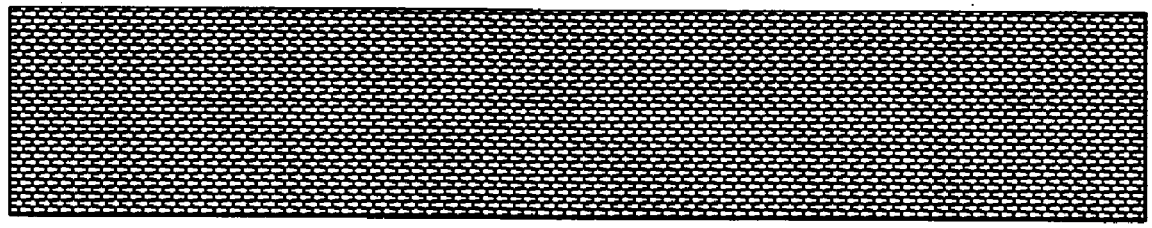
FIG. 8 is a side elevation view of a knitted fabric layer useful in the graft of the present invention.
Figure 8A:
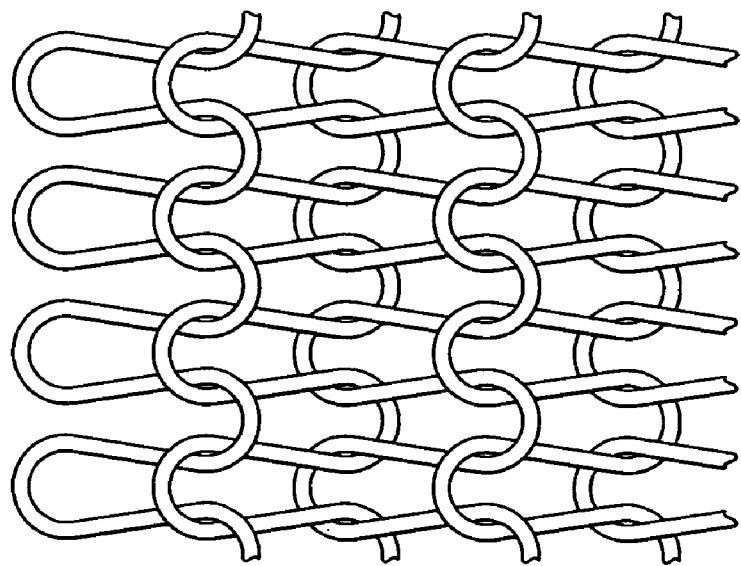
FIG. 8A is an enlarged detail of FIG. 8.

In a preferred embodiment, a knitted stretch overlay is used as the fabric layer as shown in FIGS. 8 and 8A. Knitting involves the interlooping of one yarn system into vertical columns and horizontal rows of loops called wales and courses, respectively, the fabric coming out of the machine in the wale direction.

A filament wound prosthesis, such as that described in U.S. Pat. No. 5,116,360, may also be used where fibers are drawn directly onto a rotating mandrel to form a fabric layer that is wrapped with the strands in both directions to provide a bi-axial reinforcement. In particular, as the distributor or spinnerette reciprocates along the mandrel, non-woven strands are layered on top of each other to form a porous non-woven network of criss-crossing strands. Methods for forming a filament wound prosthesis are described in U.S. Pat. No. 4,475,972.

Generally, tubular fabric layers are manufactured in a single long tube and cut to a pre-determined length. To cut the fabric layer, a laser would be desirably used, which cuts and fuses the ends simultaneously. The fabric layer is cleaned, desirably with sodium dodecyl sulfate and then rinsed with deionized water. The fabric layer can then be placed over the biodegradable layer and heat set to precisely set the diameter and to remove any creases or wrinkles. Typically, heat setting is carried out at the temperature range from about 125° C. to about 225° C. using a convection oven for a time of 20 minutes. Any known means for heating may be used. Any means of affixing the fabric layer to the biodegradable layer may be used including, but not limited to, cross-linking a biodegradable polymer in the biodegradable layer so as to bond the graft layers together.

Specifically, the composite device of the present invention may be formed by expanding a thin wall PTFE inner luminal tube at a relatively high degree of elongation, on the order of approximately between 400% and 2,000% elongation and preferably from about between 700% and 900%. The inner luminal tube is desirably expanded over a cylindrical mandrel, such as a stainless steel mandrel at a temperature of between room temperature and 640° F., preferably about 500° F. The luminal tube is preferably, but not necessarily fully sintered after expansion. Sintering is typically accomplished at a temperature of between 640° F. and 800° F., preferably at about 660° F. and for a time of between about 5 minutes to 30 minutes, preferably about 15 minutes. The resulting luminal tube formed by this method desirably exhibits an IND of greater than 40 microns, and in particular between 40 and 100 microns, most desirably between 70 to about 90 microns, spanned by a moderate number of fibrils. Such a microporous structure is sufficiently large so as to promote enhanced cell endothelization once blood flow is established through the graft. Such cell endothelization enhances the long-term patency of the graft.

The combination of the luminal ePTFE tube over the mandrel is then employed as a substrate over which the biodegradable layer can be disposed. In particular, the biodegradable layer is disposed on the external surface of the luminal ePTFE tube. In one desired embodiment, the biodegradable layer is comprised of a synthetic hydrogel polymer that can be crosslinked so as to solidify. In one embodiment, wet or fluid biodegradable material may be directly applied as a coating on the outside surface of the luminal layer by such methods as dipping, spraying or painting. A powder form of the bioactive agent can be applied to the biodegradable coating on the external surface of the luminal layer while it is still wet, or, alternatively, can be mixed with the biodegradable material before application to the external surface of the luminal layer.

As described above, the device according to the present invention further includes a fabric layer. In particular, the combination of the composite formed between the luminal ePTFE tube and the biodegradable layer is then employed as a substrate, over which the fabric layer can be disposed. Useful textile constructions include weaves, knits, braids, filament windings, spun windings and combinations thereof. Preferably, the fabric layer is a knitted stretch overlay that is applied to a wet biodegradable coating layer, such as the aforementioned synthetic hydrogel polymer. After application of the textile layer to the wet hydrogel polymer layer, the hydrogel can be crosslinked by such means as microwave or chemical crosslinking (e.g. via formaldehyde vapor) to bond the graft layers together.

The following examples serve to provide further appreciation of the invention, but are not meant in any way to restrict the scope of the invention.

EXAMPLES

Example 1

The composite device of the present invention is formed by expanding a thin wall PTFE inner luminal tube at a degree of elongation on the order of 600-900%. The inner luminal tube is expanded over a cylindrical stainless steel mandrel at a temperature of 500° F. The luminal tube is fully sintered after expansion at a temperature of 660° F. for 15 minutes. The resulting luminal tube formed by this method exhibits an IND of greater than 40 microns, and in particular between 70 and 90 microns, and is spanned by a moderate number of fibrils.

The combination of the luminal ePTFE tube over the mandrel is then employed as a substrate over which the biodegradable layer is disposed. In particular, the biodegradable layer is formed of a synthetic hydrogel polymer. The hydrogel is a water-insoluble copolymer having a hydrophilic region, at least two functional groups that will allow for cross-linking of the polymer chains and a bioresorbable hydrophobic region. Silver iodate is blended into wet hydrogel material to form a mixture which is sprayed onto the external surface of the luminal ePTFE tube.

The combination of the composite formed between the luminal ePTFE tube and the wet biodegradable coating layer is then employed as a substrate over which the fabric layer is disposed. A knitted fabric layer formed of polyester yarns capable of shrinking during a heat-set process is used. This allows the fabric layer to be heat-set on the mandrel to form a generally cylindrical shape and removes creases or wrinkles. The yarns used for the fabric layer have a denier from about 30 to about 100. In particular, the yarns are polyethylene terephthalate (PET). After knitting the fabric layer, it is cleaned and scoured in a basic solution of warm water. After rinsing to remove any remaining detergent, the fabric layer is compacted or shrunk to reduce and control the porosity of the fabric layer. The porosity of the knitted material is about 5,000 to about 17,000 when measured on the Wesolowski scale and by the procedure of Wesolowski. This porosity permits tissue ingrowth, while retaining tensile strength in the outer layer. In order to compact or shrink the fabric layer in the wale direction to obtain this desired porosity, a solution of hexafluoroisopropanol and methylene chloride is used to compact the textile layer by immersing it into the solution for 30 minutes at a temperature from about 15° C. to about 160° C. After the fabric layer has been applied to the biodegradable coating layer, the composite structure is placed in a microwave so as to crosslink the hydrogel. The crosslinking of the hydrogel serves to bond the graft layers together.

What is claimed is:

1. A vascular graft comprising:
   A luminal layer of ePTFE having an internodal distance of about 70 to about 90 microns to allow for sufficient cellular communication, wherein said luminal layer has been at least partially sintered;
   a biodegradable polymer coating comprising a hydrophilic region, at least two functional groups that will allow for cross-linking of the polymer, and a bioresorbable hydrophobic region, said coating further comprising a bioactive agent that controllably releases from the biodegradable layer to the site of implantation of the graft, said bioactive agent is a silver agent that controllably releases from the biodegradable layer to the site of implantation of the graft, said silver agent is selected from the group consisting of silver acetate, silver benzoate, silver carbonate, silver iodate, silver iodide, silver lactate, silver laurate, silver nitrite, silver oxide, silver palmitate, silver protein, silver sulfadiazine and combinations thereof, said biodegradable coating being posited directly onto the external surface of said luminal layer;
   a fabric layer posited on the external surface of said biodegradable layer, said fabric layer comprises a knitted textile construction, and
   an implantable prosthetic stent interposed between said luminal layer and said biodegradable coating,
   wherein said fabric layer has a heat-set diameter;
   wherein said bioactive agent is an antimicrobial agent;
   wherein said silver agent is not substantially absorbed into the body of the user; and
   wherein said at least partially sintered luminal layer and said heat-set fabric layer are bonded together via cross-linking of said biodegradable polymer coating.

2. The vascular graft of claim 1, wherein said fabric is of sufficient porosity to allow tissue ingrowth.

3. The vascular graft of claim 1, wherein said internodal distance of about 70 to about 90 microns allows for cellular communication between blood and perigraft tissue.

4. The vascular graft of claim 1, wherein said biodegradable coating is comprised of a natural, modified natural or synthetic polymer.

5. The vascular graft of claim 4, wherein said biodegradable coating is comprised of a synthetic hydrogel polymer.

6. The vascular graft of claim 1, wherein said bioactive agent is controllably released from said biodegradable coating to the site of implantation of said graft by hydrolysis of chemical bonds in said biodegradable polymer.

7. The vascular graft of claim 1, wherein said fabric layer is formed from synthetic yarns selected from the group consisting of polyesters, PET polyesters, polypropylenes, polyethylenes, polyurethanes, polytetrafluoroethylenes and combinations thereof.

8. The vascular graft of claim 1, further comprising an implantable stent between said luminal ePTFE layer and said biodegradable polymer coating.

9. A method of making a vascular graft for controllable delivery of a bioactive agent associated therewith to a site of implantation of said graft, said method comprising:

providing a luminal layer of ePTFE with an internodal distance of about 70 to about 90 microns to allow for sufficient cellular communication;

positing a biodegradable polymer coating comprising a hydrophilic region, at least two functional groups that will allow for cross-linking of the polymer, and a bioresorbable hydrophobic region, said coating comprising a bioactive agent graft, said bioactive agent is a silver agent that controllably releases from the biodegradable layer to the site of implantation of the graft, said silver agent is selected from the group consisting of silver acetate, silver benzoate, silver carbonate, silver iodate, silver iodide, silver lactate, silver laurate, silver nitrite, silver oxide, silver palmitate, silver protein, silver sulfadiazine and combinations thereof, and positing said coating directly on the external side of said luminal layer;

positing a fabric layer on the external surface of said biodegradable layer, said fabric layer comprising a knitted textile construction; heat-setting said fabric layer at a temperature of from about 125° C. to about 225° C. and crosslinking said biodegradable polymer coating after the positing of said fabric layer so as to bond said luminal layer, said biodegradable coating, and said fabric layers together; wherein said bioactive agent is an antimicrobial agent, and interposing an implantable prosthetic stent between said luminal layer and said biodegradable coating, 10. The method of claim 9, further comprising the step of incorporating said bioactive agent into said coating.

11. The method of claim 9, wherein said crosslinking is via microwave or chemical crosslinking.

12. The method of claim 9, wherein said biodegradable coating is comprised of a synthetic hydrogel polymer.

13. The method of claim 9, wherein said bioactive agent is controllably released from said biodegradable coating to the site of implantation of said graft by hydrolysis of chemical bonds in the biodegradable polymer.

14. The method of claim 13, wherein said fabric layer is of a porosity to allow sufficient tissue ingrowth to replace said biodegradable polymer following said hydrolysis.

15. The method of claim 9, wherein said fabric layer is formed of synthetic polyester yarns.

16. The method of claim 9, wherein said fabric layer comprises a textile construction selected from the group consisting of weaves, knits, braids, filament windings, spun fibers and combinations thereof.

17. An implantable device for arterial-venous access comprising:

a luminal layer of ePTFE having an internodal distance of about 70 to about 90 microns to allow for sufficient cellular communication, wherein said luminal layer has been at least partially sintered;

a biodegradable polymer coating comprising a hydrophilic region, at least two functional groups that will allow for cross-linking of the polymer, and a bioresorbable hydrophobic region, said coating comprising a silver agent that controllably releases from the biodegradable layer to the site of implantation of the graft, said silver agent is selected from the group consisting of silver acetate, silver benzoate, silver carbonate, silver iodate, silver iodide, silver lactate, silver laurate, silver nitrite, silver oxide, silver palmitate, silver protein, silver sulfadiazine and combinations thereof, said biodegradable layer being posited directly onto the external surface of said luminal layer;

a fabric layer posited on the external surface of said biodegradable layer, said fabric layer comprises a textile construction selected from the group consisting of weaves, knits, braids, filament windings, spun fibers and combinations thereof; and an implantable prosthetic stent interposed between said luminal layer and said biodegradable coating;

wherein said fabric layer has a heat-set diameter;

wherein said silver agent is not substantially absorbed into the body of the user; and wherein said at least partially sintered luminal layer and said heat-set fabric layer are bonded together via cross-linking of said biodegradable polymer coating.

18. The device of claim 17 wherein said silver agent prevents bacteria from adhering or growing on said device.

19. The device of claim 17, wherein said biodegradable layer is comprised of a synthetic hydrogel polymer.

20. The device of claim 19, wherein said synthetic hydrogel polymer has a swelling capacity of up to 300%.

21. The device of claim 20, wherein said silver agent is controllably released from said biodegradable layer to the site of implantation of said graft by hydrolysis of chemical bonds in the biodegradable polymer.

* * * * *